United States Patent [19]

Redmore et al.

[11] 4,005,160

[45] Jan. 25, 1977

[54] PREPARATION OF α-AMINO PHOSPHONIC ACID DERIVATIVES

[75] Inventors: Derek Redmore, Ballwin; Neil E. S. Thompson, Creve Coeur, both of Mo.

[73] Assignee: Petrolite Corporation, St. Louis, Mo.

[22] Filed: May 5, 1975

[21] Appl. No.: 574,262

[52] U.S. Cl. .............................. 260/970; 260/502.5; 260/944

[51] Int. Cl.² ............................................ C07F 9/40

[58] Field of Search .................... 260/970, 502.5

[56] References Cited

UNITED STATES PATENTS 2,971,019  2/1961  Ladd et al. ................... 260/970 X
3,048,613  8/1962  Ladd et al. ................... 260/970 X

OTHER PUBLICATIONS

Sidgwick, "The Organic Chemistry of Nitrogen," (1949), p. 16, Clarendon Press, Oxford.
Kosolapoff, "Organo Phosphorus Compounds," (1950), J. Wiley & Sons, New York, pp. 232–233.

Primary Examiner—Anton H. Sutto
Attorney, Agent, or Firm—Sidney B. Ring; Hyman F. Glass

[57] ABSTRACT

This invention relates to a process for preparing α-amino phosphonic acid derivatives which comprises reacting a nitrile with a phosphite ester under hydrogenation conditions; and to the α-amino phosphonic acid derivatives formed and uses thereof.

11 Claims, No Drawings

PREPARATION OF α-AMINO PHOSPHONIC ACID DERIVATIVES

Previous methods for the preparation of α-amino phosphonic acid derivatives required complicated reactions involving many steps and the use of sophisticated reagents.

We now have discovered a process for the preparation of α-amino phosphonic acid derivatives by a process which comprises reacting nitriles under hydrogenation conditions.

The key step in our process is the generation of an imine, R—CH=NH, in presence of a phosphite

so that the phosphite adds to the imine to form a C-P bond. The imine is generated by hydrogenation of a nitrile. Thus the process is simply hydrogenation of a nitrile in presence of a phosphite.

The equation 1 summarizes the process:

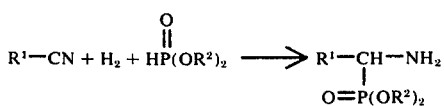

The product A can react further via its primary amino group adding to further imine formed in the reduction process. This step is shown in equation 2.

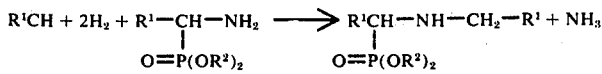

An additional possibility is that the imine is further reduced without being intercepted by phosphite or by α-amino phosphonate yielding the simple amine $R_1CH_2NH_2$ as shown in equation 3.

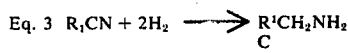

In practice products A, B and C are all found. The whole process is summarized below:

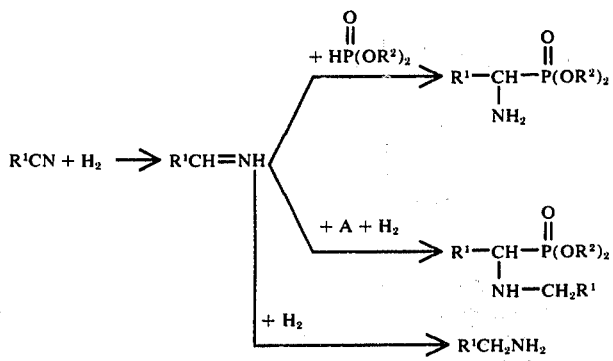

In principle any catalyst which is capable of bringing about reduction of a nitrile can be used in this process. Such catalysts include platinum, palladium, rhodium on various supports, Raney nickel, etc. The phosphites exert a modifying effect to the catalytic activity of the catalysts to varying degrees. In general the reduction process is significantly slower in presence of the phosphite. The preferred catalyst for this process is Raney nickel.

The reduction process can be carried out on mixtures of nitrile and phosphite in various ratios with or without solvent. Suitable solvents include hydrocarbons such as hexane, cyclohexane, benzene, toluene, etc.; alcohols such as methanol, ethanol, butanol, isopropanol, etc.; ethers such as tetrahydrofuran. The ratio of nitrile to phosphite can vary from 1:1 to 1:10 or higher. With higher amounts of phosphite yields of product A increase and amounts of C significantly decrease.

The reaction conditions can vary widely depending on the particular system actually employed. For example, the reduction process can be carried out at temperatures from 20° C. to 150° C. and hydrogen pressures from 40 to 2000 psi. The preferred conditions are 30°–100° C. and pressures from 100 to 1000 psi of hydrogen.

The process is applicable to a wide range of nitriles for example aliphatic nitriles such as acetonitrile, propionitrile, butyronitrile, lauric acid nitrile, stearonitrile; aryl nitriles such as toluonitriles, chlorobenzonitrile; or heterocyclic nitriles such as nicotinic acid nitrile, isonicotinic acid nitrile, etc. Compounds bearing more than one nitrile group can be employed such as aliphatic dinitriles such as malononitrile, glutaronitrile, adiponitrile, etc.; aryl dinitriles such as phthalonitrile, etc. Polymers or copolymer nitriles can also be utilized such as polyacrylonitrile, polymethacrylonitrile, or copolymers of acrylonitrile or methacrylonitrile with vinyl monomers such as ethylene, styrene, vinyltoluene, etc.

The phosphite component includes virtually all phosphites of the general formula

where $R^2$ and $R^3$ are alkyl, aryl, aralkyl or where $R^2$ and $R^3$ form a ring. Examples include dimethyl phosphite, diethyl phosphite, dipropylphosphite, diisopropyl phosphite, dibutyl phosphite, dilauryl phosphite, dioctylphosphite, diphenylphosphite, di-p-tolyl phosphite, etc.

Cyclic phosphites include:

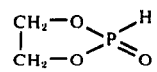
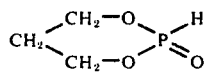
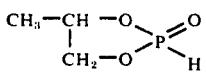
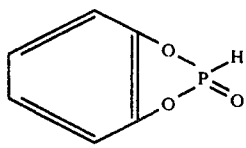

The phosphonate esters A and B can be readily hydrolysed, for example, with acid or base to yield the corresponding phosphonic acids.

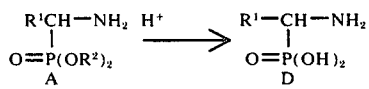
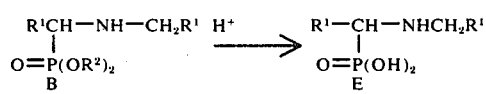

In cases where R¹ is aryl the product E is readily converted into D by hydrogenolysis.

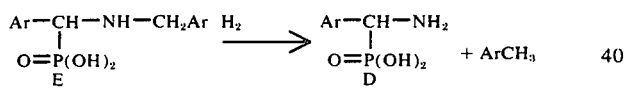

The relative simplicity of the present process is unexpected since previous routes to products A and D have required numerous steps and sophisticated reagents.

The following examples are presented by way of illustration and not of limitation.

EXAMPLE 1

To a solution of benzonitrile (75g; 0.73 mole) in diethyl phosphite (200g; 1.45 mole) was added W-2 Raney nickel (6g) and the whole mixture charged in an autoclave. The reactor was pressured to 600 psi with hydrogen and the mixture heated to 60° C. The pressure was maintained at 550–600 psi by addition of hydrogen as the reduction proceeded. After 18 hours, uptake of hydrogen had ceased. After cooling hydrogen was released and the catalyst filtered as the reaction product was removed from the reactor. Excess diethyl phosphite and unreacted benzonitrile was removed (135g) by distillation under reduced pressure. The residue was diethyl N-benzyl α-aminobenzylphosphonate. Hydrolysis of this residue with 18% HCl after crystallization yielded N-benzyl α-amino benzylphosphonic acid, 83g (82%), mp 233°–6°.

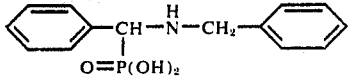

Analysis. Found N, 4.91; P, 11.05.
Calculated for $C_{14}H_{16}NO_3P$: N, 5.05; P, 11.18.
Nmr spectrum was in accord with the assigned structure.

EXAMPLE 2

This example illustrates formation of diethyl α-amino benzylphosphonate as the major reaction product.

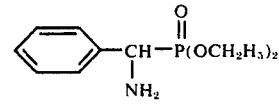

Into an autoclave were charged benzonitrile (90g; .88 mole), diethyl phosphite (250g; 1.8 mole) and W-2 Raney nickel (5g). The mixture was heated at 87°–90° under a hydrogen pressure of 170–200 psi for 18 hours. The catalyst was filtered and the product freed from excess diethyl phosphate and unreacted benzonitrile by heating at 70° under reduced pressure. A small amount of solid formed which was filtered and discarded. Pure diethyl α-amino benzylphosphonate was obtained from the resulting liquid as follows. Dry hydrochloric acid gas was passed into crude product for 2 hours followed by addition of ether. The resulting solid was filtered and after crystallization from ethanol/ether gave pure diethyl α-amino benzylphosphonate hydrochloride mp 135°–140°, 37g. Nmr spectrum indicated pure sample.

Analysis: Found: N, 4.85; P, 10.80; Cl, 13.06; eq. wt. 283 Calculated for $C_{11}H_{19}NO_3PCl$: N, 5.01; P, 11.09; Cl, 12.70, eq. wt. 279.5.

EXAMPLE 3

This example illustrates the use of a solvent. To a solution of m-toluonitrile (58.5g; 0.5 mole) and diethyl phosphite (70g; 0.51 mole) in cyclohexane (200 ml) in an autoclave was added Raney nickel (10g). The solution was heated to 60° and pressured to 600 psi with hydrogen. Heating was continued at 55°–60° with hydrogen pressure maintained at 500–600 psi by repressuring as necessary. After 24 hours hydrogen uptake had ceased. Solvent and unreacted starting materials were removed by distillation under reduced pressure to yield 110g of crude ester.

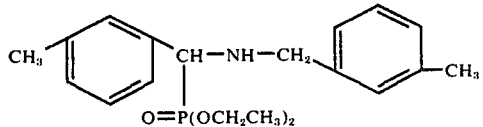

Hydrolysis of this crude ester with 18% hydrochloric acid yielded the corresponding acid, mp. 233°–5°.

Analysis, calculated for $C_{16}H_{20}NO_3P$; N, 4.59; P, 10.16. Found: N, 4.65; P, 9.70.

EXAMPLE 4

In autoclave was charged o-chlorobenzonitrile (50g; 0.365 mole), diethyl phosphite (220g; 1.6 mole) and Raney nickel (10g). The mixture was reduced under a hydrogen pressure of 530–600 psi at 57°–62° for 20 hr. at which time hydrogen uptake had ceased. Unreacted phosphite and nitrile were removed from the reaction mixture after filtration of the catalyst. The resulting crude ester was hydrolysed with 18% hydrochloric acid to yield a white solid. Recrystallization from aqueous acetic acid yield pure N(2-chlorobenzyl)-α-amino 2-chlorobenzylphosphonic acid mp 205°–7°.

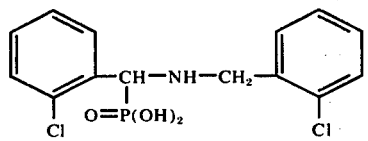

Analysis: calculated for $C_{11}H_{14}Cl_2NO_3P$: N, 4.05; P, 8.96. Found: N, 3.95; P, 8.63.

EXAMPLE 5

The use of an aliphatic nitrile.

A solution of propionitrile (27.5g; 0.5 mole) and diethyl phosphite (70g; 0.51 mole) in cyclohexane (200 ml) was reduced in presence of Raney nickel (10g) at 55°–60° and hydrogen pressure of 560–600 psi. Uptake of hydrogen ceased after 6 hours. Unreacted starting materials and solvent were removed by distillation to yield 20g of crude ester. This was further purified by dissolving in ether and saturating the solution with HCl whereupon the hydrochloride of diethyl N-propyl α-aminopropylphosphonate separated.

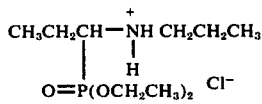

This product was characterized by its nmr spectrum. Hydrolysis of this ester yielded N-propyl α-aminopropylphosphonic acid as a hydroscopic oil. The nmr spectrum was consistent with the assigned structure.

EXAMPLE 6

A solution of benzonitrile (52g; 0.5 mole) and dibutyl phosphite (38.8g; 0.2 mole) in cyclohexane (200 ml) was hydrogenated at 500–600 psi of hydrogen at 55°–57° in presence of Raney nickel (10g) for 24 hrs. Removal of solvent yielded an oil which contained a significant amount of unreacted nitrile. Saturation with anhydrous HCl gas led to separation of an oil 40g (50%) shown by nmr to be dibutyl N-benzyl α-aminobenzylphosphonate hydrochloride. Hydrolysis of a portion of this ester gave N-benzyl α-aminobenzylphosphonic acid identical to that of Example 1.

EXAMPLE 7

This example illustrates the use of an aryl phosphite.

A solution of benzonitrile (52g; 0.5 mole) and diphenyl phosphite (160g; 0.7 mole) in cylcohexane (150 ml) was hydrogenated in presence of Raney nickel (8g) at 60°–65° and 500–600 psi of hydrogen. After 18 hrs. hydrogen uptake ceased and after cooling the catalyst was filtered. Evaporation of solvent yielded crude product containing unreacted benzonitrile and diphenyl phosphite. Chromatography on alumina from benzene yielded by elution with chloroform/benzene diphenyl N-benzyl α-aminobenzylphosphonate as an oil. IR and Nmr were consistent with the assigned structure.

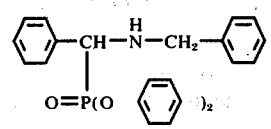

The compositions of this invention have a wide variety of uses. They are particularly useful as
Scale inhibitors,
Corrosion inhibitors — particularly for oxygen containing systems, and as
Chelating agents.

We claim:
1. A process of preparing an α-aminophosphonic acid derivative which comprises reacting a nitrile with a phosphite ester of the general formula

where $R^2$ and $R^3$ are alkyl, aryl, aralkyl or where $R^2$ and $R^3$ together form a ring structure in a ratio of nitrile to phosphite of about 1:1 to about 1:10 or more at a temperature from about 20° C. to about 150° C. and hydrogen pressures of about 40 to about 200 psi under hydrogenation conditions.

2. The process of claim 1 where the α-aminophosphonic acid derivatives formed comprise those of the formula

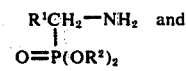

$$R^1CH_2-NH-CH_2-R^1$$
$$O=P(OR^2)_2$$

where $R^1$ is a hydrocarbon group and $R^2$ is a hydrocarbon group.

3. The process of claim 2 where $R^1$ is an arylic group.
4. The process of claim 3 where the arylic group is a phenyl or a substituted phenyl group.
5. The process of claim 4 where

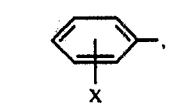

where X is hydrogen, alkyl, halogen or combinations thereof.

6. The process of claim 2 where $R^1$ is aliphatic.
7. The process of claim 1 where an additional step of hydrolization is carried out to produce an α-aminophosphonic acid.
8. The process of claim 7 where the hydrolysis is carried out using hydrochloric acid.

9. The process of claim 7 where the α-aminophosphonic acids formed comprise those of the formula
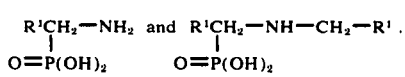
10. The process of claim 1 where the nitrile m-toluonitrile and the phosphite ester is diethyl phosphite.
11. The process of claim 7 where the nitrile is m-toluonitrile, the phosphite ester is diethyl phosphite and the final product obtained is
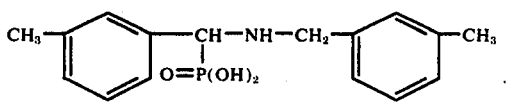
* * * * *